United States Patent [19]

Kesling

[11] Patent Number: 4,842,514
[45] Date of Patent: Jun. 27, 1989

[54] UPRIGHTING SPRING

[75] Inventor: Peter C. Kesling, LaPorte, Ind.

[73] Assignee: TP Orthodontics, Inc., Westville, Ind.

[21] Appl. No.: 141,587

[22] Filed: Jan. 7, 1988

[51] Int. Cl.⁴ ............................................. A61C 7/00
[52] U.S. Cl. ....................................... 433/21; 433/18
[58] Field of Search .................................. 433/18, 21

[56] References Cited

U.S. PATENT DOCUMENTS

| | | |
|---|---|---|
| 3,093,903 | 6/1963 | Kesling . |
| 3,633,277 | 1/1972 | Reichol .............................. 433/21 |
| 3,641,672 | 2/1972 | Kesling .............................. 433/21 |
| 3,686,758 | 8/1972 | Kesling . |
| 3,793,730 | 2/1974 | Begg et al. . |
| 4,350,487 | 9/1982 | Kesling et al. . |

OTHER PUBLICATIONS

American Orthodontics Catalog X 1986, p. 79.

Primary Examiner—Robert Peshock
Attorney, Agent, or Firm—Lloyd L. Zickert

[57] ABSTRACT

An uprighting spring for use with an edgewise and/or ribbon arch type bracket wherein the spring includes, a coil or force-generating portion adapted to be disposed on the labial surface of the bracket, a tail to be anchored in a vertical opening or slot of the bracket or to a tie wing of an edgewise bracket, and means connected to the coil portion and adaptable to extend substantially along the archwire and be connected to the archwire when activating the spring.

26 Claims, 3 Drawing Sheets

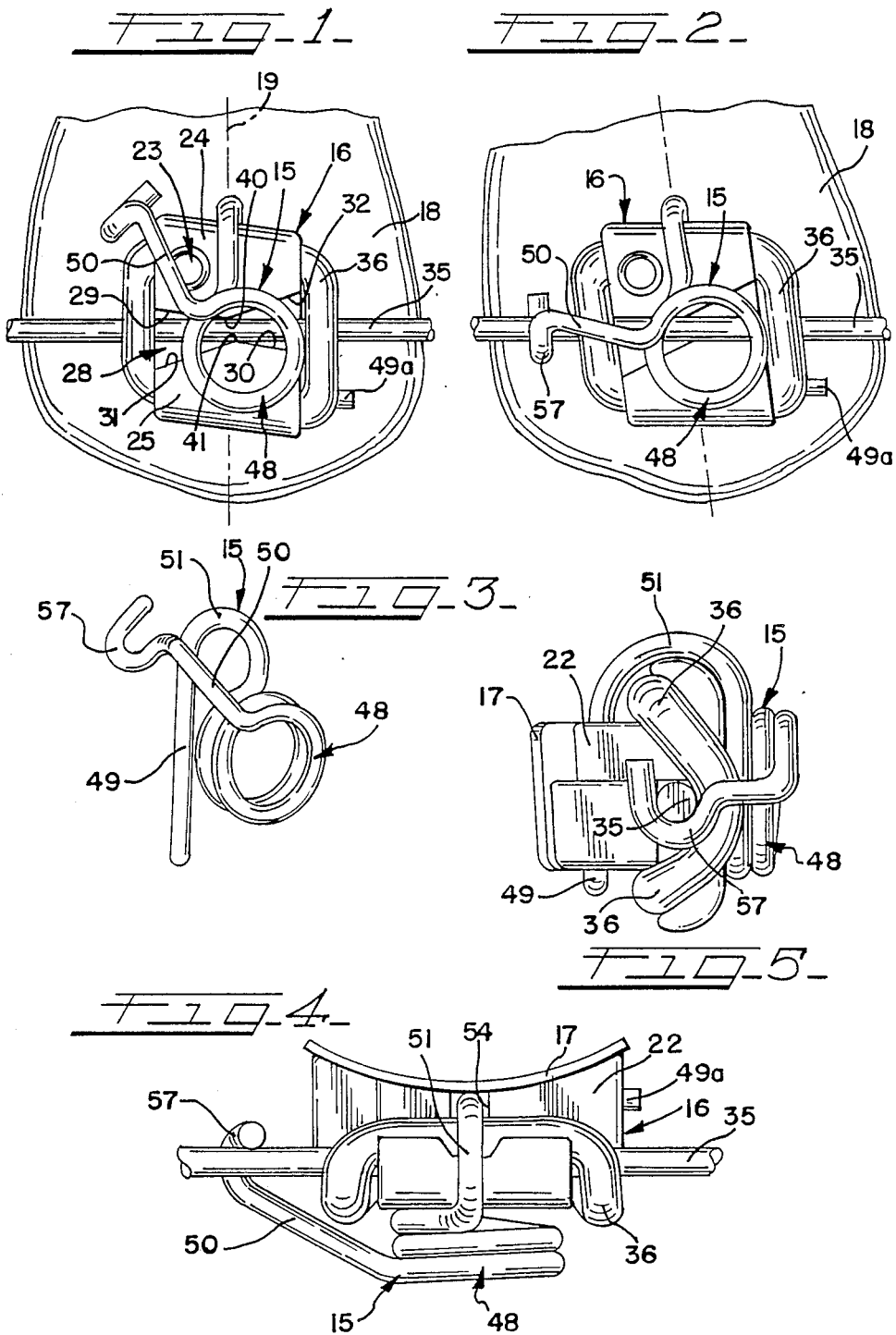

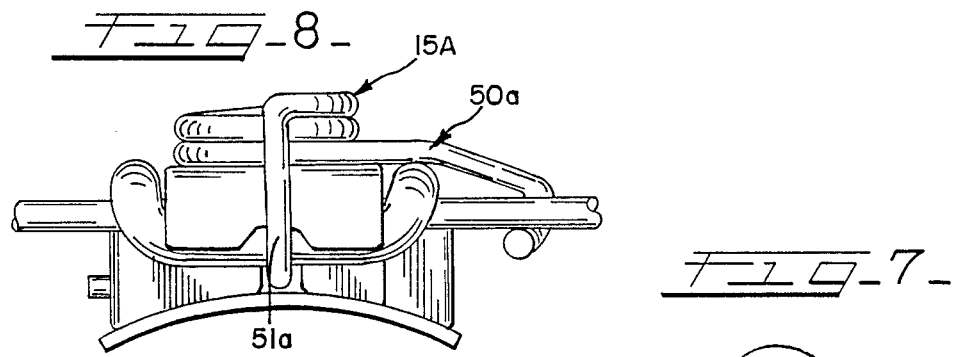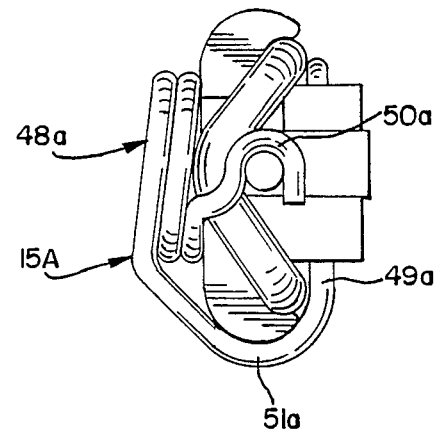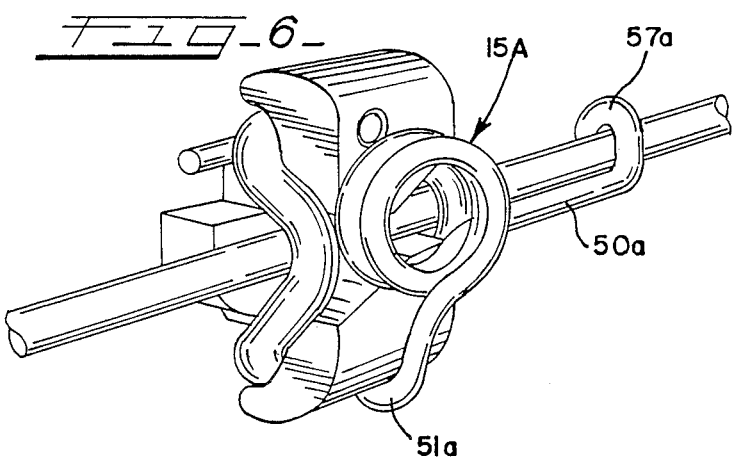

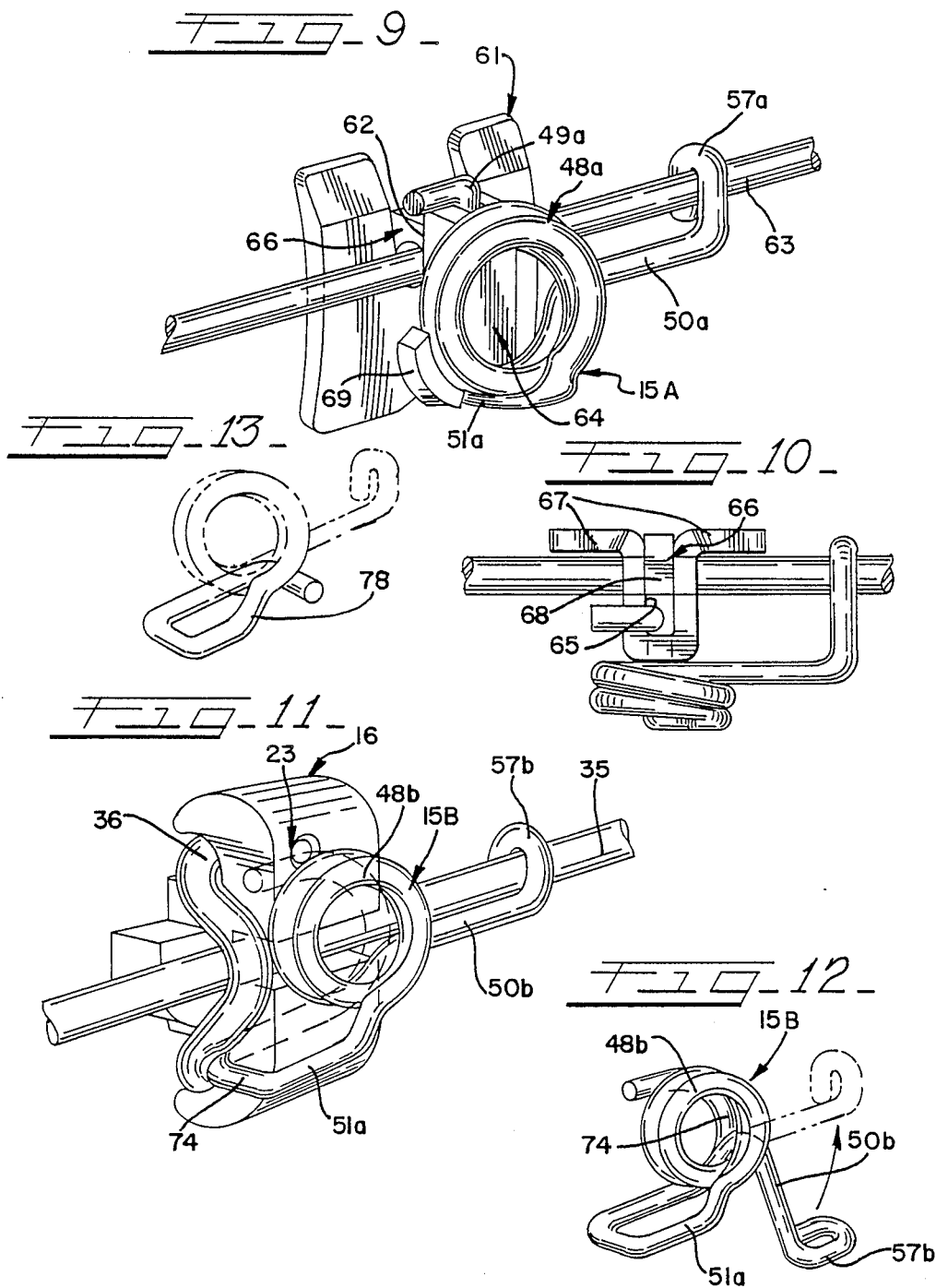

UPRIGHTING SPRING

DESCRIPTION

This invention relates in general to an uprighting spring for use with an orthodontic bracket of the edgewise or ribbon arch type wherein the coil or force-generating portion of the spring is disposed at the labial of the bracket to blend in with the labial profile of the bracket and also to enhance hygiene.

BACKGROUND OF THE INVENTION

Heretofore, it has been well known to provide uprighting springs for orthodontic brackets which coact with the bracket and archwire for purposes of producing an uprighting movement to the bracket and tooth. These uprighting springs have commonly included a coil section for generating a force. One end of the coil is connected to a tail or leg that is adapted to be received in a vertical opening of the bracket for anchoring the spring or to a hook for engaging a tie wing tip of an edgewise bracket, and the other end of the coil is connected to a lever arm having a hook that is adapted to hook onto the archwire when activating the spring.

Heretofore known uprighting springs have usually disposed the coil section at the gingival or occlusal end of the bracket where it lies against the enamel surface of the tooth or is in close proximity to the enamel surface of the tooth whereby food and the like can be trapped between it and the tooth surface which contributes to poor hygiene. Moreover, the location of the coil section at the gingival or occlusal ends of the bracket increases the overall profile of the bracket making it more unsightly. A typical uprighting spring of this type is illustrated in FIG. 7 of U.S. Pat. No. 4,350,487 and in U.S. Pat. No. 3,093,903.

SUMMARY OF THE INVENTION

The present invention overcomes the hygienic and profile disadvantages of the prior art known springs in providing an uprighting spring that disposes the coil or force-generating portion at the labial of the orthodontic bracket which is much more hygienic and more aesthetically pleasing. The spring of the present invention reduces the overall labial profile of the appliance.

The term "and/or" used herein is intended to cover three alternatives. For example, "edgewise and/or ribbon arch type bracket" means an edgewise and ribbon arch type bracket, or an edgewise type bracket, or a ribbon arch type bracket. Combination edgewise and ribbon arch type brackets are well known, as are edgewise and edgewise type brackets and ribbon arch and ribbon arch type brackets. The term "coil section" is intended to include a coil shaped section having one or more turns, or a force-generating section.

It is therefore an object of the present invention to provide a new and improved uprighting spring for an orthodontic bracket of the edgewise and/or ribbon arch type.

It is a further object of the present invention to provide a new and improved uprighting spring for an orthodontic bracket which disposes the coil section at the labial of the bracket, thereby improving hygienic conditions and reducing the overall labial profile to make the appliance more aesthetically pleasing.

Other objects, features and advantages of the invention will be apparent from the following detailed disclosure, taken in conjunction with the accompanying sheets of drawings, wherein like reference numerals refer to like parts.

DESCRIPTION OF THE DRAWINGS

FIG. 1 is a front elevational view of a tip-edge or edgewise type bracket mounted on a tooth and having an uprighting and tipping slot and illustrating the uprighting spring of the present invention mounted on the bracket with the lever arm in disengaged position;

FIG. 2 is a view similar to FIG. 1 but showing the lever arm of the uprighting spring in engaged position with the archwire and the resultant uprighting of the tooth;

FIG. 3 is a perspective view of the uprighting spring shown in FIGS. 1 and 2;

FIG. 4 is a top plan view of the spring as mounted on the bracket and in engagement with the archwire;

FIG. 5 is an end elevational view of the combination bracket spring and archwire components and looking at the lever arm end of the spring;

FIG. 6 is a pespective view of a modified uprighting spring according to the invention mounted on an edgewise bracket and showing it in association with an archwire and which differs from the spring of FIGS. 1 and 5 in that the connecting portion to the tail or leg is labial to the activating coil and is mounted over the occlusal end of the bracket;

FIG. 7 is an end elevational view of the assembly in FIG. 6 and taken from the activating arm end of the spring;

FIG. 8 is an occlusal view of the assembly shown in FIG. 6;

FIG. 9 is a perspective view of an assembly including a ribbon arch bracket and the uprighting spring of the present invention of the type shown in the embodiment of FIGS. 6 to 8;

FIG. 10 is a gingival view of the assembly shown in FIG. 9;

FIG. 11 is a perspective view of another modified uprighting spring mounted on an edgewise type bracket which differs from the embodiments of FIGS. 1 to 8 in that the tail or anchoring portion is formed to hook or engage behind the tie wing tips;

FIG. 12 is a perspective view of the spring of FIG. 11 as it would appear before mounting on a bracket; and FIG. 13 is a fragmentary perspective view of a modification that differs from the embodiment of FIGS. 11 to 12 in that the tail engages a single wing tip.

DESCRIPTION OF THE INVENTION

The uprighting spring of the invention is illustrated in FIGS. 1 to 8, 11 and 12 for use with an edgewise type bracket and in FIGS. 9 and 10 for use with a ribbon arch or Begg bracket. However, it should be appreciated that the spring could be used with any bracket where tipping or uprighting movement can be achieved between the bracket and the archwire, including a combination edgewise and ribbon arch bracket, or a standard edgewise bracket with one or more tie wings and using a small wire in the slot. It is also understood that the bracket on which the uprighting spring embodiments of FIGS. 1 to 8 would be mounted would have a vertical or occlusogingivally extending opening in which the tail or leg of the spring, formed as a straight section, could be anchored. The spring embodiment of FIGS. 11 and 12 could be mounted on any edgewise or edgewise type bracket having at least one tie wing.

The uprighting spring of the invention would normally be made of a suitable metal having the spring characteristics desired, although it should be appreciated that it could be made of any other suitable material having a resiliency or flexibility that would tend to generate a force to return to its normal unactivated position.

The uprighting spring embodiment illustrated in FIGS. 6 to 8 differs from that illustrated in FIGS. 1 to 5 in that the tail or leg which anchors one end of the coil section to the bracket is connected to the labial side of the coil section. It will also be understood that the springs or either embodiment may have the tail inserted from the opposite side illustrated. The embodiment of FIGS. 11 and 12 differs from the embodiments of FIGS. 1 to 8 in that the tail is formed so that it can be connected to a tie wing. FIG. 13 differs from the embodiment of FIGS. 11 and 12 in that the tail only engages a single tie wing tip. In all embodiments, one end of the coil or force-generating portion is anchored to the bracket and the other end is connected to the archwire to produce movement between the bracket and the archwire.

The spring in FIGS. 1 to 5 is generally designated as 15 and is mounted on a bracket 16 that is in turn suitably mounted on a base 17 which is suitably bonded or otherwise secured to the labial surface of a tooth 18. In FIGS. 1 and 2 bracket 16 is mounted on an upper right canine tooth and is in alignment with the long axis 19 of the crown. The bracket and tooth in FIG. 1 is illustrated as being oriented in an undesired position; while in FIG. 2 where uprighting has taken place, the tooth is shown oriented in the ideal uprighted position.

The bracket 16 is a Tip Edge bracket or an edgewise type and is like that disclosed in my copending U.S. patent application Ser. No. 054,837 filed June 4, 1987. "Tip Edge" is a trademark owned by TP Orthodontics, Inc. of Westville, Ind. This bracket includes a body 22 having a tie wing 23 which includes an upper or gingival tie wing tip 24 and a lower occlusal tie wing tip 25. Centrally disposed of the tie wing is an archwire slot 28 opening horizontally and having diagonally opposed uprighting stops 29 and 30. Opposing the uprighting stops 29 and 30 and also in diagonal positions are tipping stops 31 and 32 which together with the uprighting stops define a substantially propeller shaped opening. The tipping stops 31 and 32 may function to limit crown tipping movement, while the uprighting stops 29 and 30 limit uprighting movement. The surfaces of the stops are illustrated as being flat, although they may take any desired form and serve as uprighting and tipping stops. Thus, the bracket will accommodate crown tipping and root uprighting movements.

As seen particularly in FIGS. 1 and 2, the archwire slot 28 is formed to receive an archwire 35 of the usual type used for tipping and uprighting functions. The archwire 35 is illustrated as being round wire, although it should be appreciated that it could be rectangular wire. While the archwire 35 is illustrated to substantially fill the archwire slot as defined by the pivot edges 40 and 41, it will be appreciated that an orthodontist might desire to use a slightly smaller sized wire depending upon the objectives sought. The archwire 35 would normally be disposed generally parallel to the occlusal plane of the dental arch particularly in connection with practicing the straight-wire technique. The archwire 35 is suitably retained in the bracket slot by means of a ligature, and an elastic ligature 36 is illustrated which comes over the outside of the wire at the opposite sides of the bracket and is hooked back of the upper and lower tie wing tips, as seen particularly in FIGS. 1, 2, 4 and 5. It may be appreciated that other types of ligatures may be used to secure the archwire to the bracket.

Relative movement between the archwire 35 and the bracket 16 will be about pivot edges or areas 40 and 41 which are slightly offset from each other and on opposite sides of the axis 19. Further, these pivot edges are disposed between the stops with the pivot edge 40 being disposed between the uprighting stop 29 and the tipping stop 32 and pivot edge 41 being disposed between the uprighting stop 30 and the tipping stop 31. Thus, the pivot edges will function as a fulcrum about which the bracket will pivot on the archwire 35.

Once the desired tipping movement has been accomplished, the next objective is to upright the root of the tooth, and the uprighting spring 15 of the present invention when mounted on the bracket and associated with the archwire will apply an uprighting force between the archwire and the bracket and therefore an uprighting movement to the tooth on which the bracket is mounted. The spring 15 generally includes a force-generating section in the form of a power coil 48 having one or more turns, an anchoring leg or tail 49 in the form of a straight section for anchoring one end of the power coil 48 to the bracket, and a lever arm 50 for connecting the other end of the power coil to the archwire, thereby setting up an uprighting force between the archwire and the bracket. The tail 49 is interconnected to one end of the power coil by means of an intermediate and generally arcuately shaped connecting section 51 which, as seen in FIGS. 1, 2, 4 and 5, is disposable over the upper tie wing tip 24. The leg or tail 49 is received in a vertical slot or opening 54 formed in the bracket body 22 lingual to or at the back side of the archwire slot 28. The vertical opening is centrally disposed in the body, and the body together with the base 17 forms an occlusogingivally extending opening in which the spring tail 49 is received. The length of the tail 49 is preferably such that it can be bent over the occlusal end of the bracket as seen by the terminal end 49a in FIGS. 1, 2 and 4. However, it should be appreciated that the force generated in an activated spring would normally maintain the tail 49 in the vertical slot 54 of the bracket.

The uprighting spring 15 is illustrated in FIG. 3 prior to being inserted into an opening of the bracket and in FIG. 1 as initially mounted on the bracket with the terminal end 49a of the tail 49 being bent over the underside or occlusal side of the bracket body to prevent removal of the tail from the bracket slot.

The terminal end of the spring lever arm 50 includes a hook 57 to facilitate the interconnection of the spring to the archwire. Following the mounting of a spring on a bracket and the bending over of the end portion of the tail, the spring is activated by forcing the lever arm downwardly and then allowing the hook 57 to hook over the archwire 35, as seen in FIG. 2, and complete the installation of the spring. The counter-clockwise force generated by the spring 15 is one that causes the bracket and tooth to move in an uprighting direction until the stops 29 and 30 seat on the archwire 35, as seen in FIG. 2.

It will now be appreciated, as seen in FIGS. 1 and 2, that the power coil 48 of the uprighting spring 15 is disposed on the labial side of the bracket 16 which is away from the enamel surface of the tooth 18. Thus, the spring 15 precludes the trapping of food particles between the power coil and the enamel surface of the teeth, thereby providing more hygienic conditions within the mouth. Additionally, it can be seen that with the coil 45 disposed on the outer face or labial of the bracket and the lever arm 50 to be substantially in alignment with the archwire 35 when the spring is activated, the lever arm 50 will be substantially in horizontal alignment with the archwire 35 which thereby additionally reduces the overall labial profile of the bracket to enhance appearance, as seen particularly in FIG. 2.

The spring embodiment in FIGS. 6 to 8 differs from that in FIGS. 1 to 5 principally in that the power or lever arm 50a is connected to the power coil at the lingual side of the power coil as opposed to being at the labial side and the tail is connected through interconnecting section 51a to the labial or buccal side of the power coil. More specifically, this uprighting spring is generally designated by the numeral 15A which includes a power coil 48a of one or more turns, a tail or leg 49a, a lever arm 50a, an intermediate connecting portion 51a between the tail and the power coil, and a hook 57a at the terminal end of the lever arm 50a. Otherwise, spring 15A functions substantially identically to the spring 15. Additionally, the disposition of section 51a labial to the coil serves to protect against damage to the coil that may be caused by chewing action from the opposing teeth. Thus, spring 15A would better maintain coil integrity.

The ribbon arch or Begg bracket 61 in FIGS. 9 and 10 is like that disclosed in my U.S. Pat. No. 3,445,933 and differs primarily from the edgewise type bracket shown in FIGS. 1 to 8 in that it includes a vertical archwire slot 62 for receiving the archwire 63. It is well known that this bracket will accommodate crown tipping and root uprighting movements. Bracket 61 includes a body 64 having a vertically or occlusogingivally extending opening 65 for not only receiving an archwire lock pin for locking the archwire 63 to the bracket as illustrated by lock pin 66 but also for receiving anchoring portions of other auxiliaries such as an uprighting spring. It will be further appreciated that the body includes at the lingual side of a pair of attaching flanges 67 which may be suitably secured to a base that can be directly bonded to a tooth surface or otherwise connected to a tooth surface through a band. As illustrated, the lock pin includes a lock pin head 68 which overlies the archwire after it is first inserted into the archwire slot to thereby lock the archwire in place and a tail 69 that can be bent over the underside of the bracket to firmly hold the archwire in place. The head of the lock pin is such as to leave an opening labially or at the front side of the archwire which then can receive the tail of the uprighting spring. Inasmuch as the uprighting spring illustrated in use with the ribbon arch bracket is of a type substantially like spring 15A shown in FIGS. 6 to 8, the same legends used for spring 15A will be used in FIGS. 9 and 10. Thus, the power coil 48a is disposed on the labial or front side of the bracket 61 with the tail 49a received in the vertical opening 65 of the bracket body 64 and the interconnecting section 51a positioned over the bottom or occlusal end of the bracket. It should be appreciated that the upper end of bracket 61 as illustrated is normally facing gingivally. The terminal end of the tail may likewise be bent over the end of the bracket to securely lock the anchoring end of the spring to the bracket. Further, the hook 57a of the lever arm 50a is disposed over the archwire 53 in a fashion to cause a counterclockwise uprighting movement between the archwire 63 and the bracket 61. The lever arm 50a also is substantially disposed in alignment with the archwire 63 to additionally mask the visual observance of the lever arm and enhance the aesthetics of the appliance. The spring 15A as mounted in FIGS. 9 and 10 thereby functions to produce an uprighting force between the archwire 63 and the bracket. It should be recognized that the tail may be inserted in the bracket opening either gingivally or occlusally, and further that a spring of the type in FIGS. 1 to 5 may be used.

As mentioned before, the uprighting spring embodiment of FIGS. 11 and 12 differs from the embodiments of FIGS. 1 to 8 in that one end of the coil is attached to a tie wing of the bracket rather than being received in a vertical slot of the bracket. This uprighting spring is generally designated as 15B and includes a power coil 48b, a lever arm 50b extending from one end of the coil and terminating in a hook 57b for engaging the archwire 35, and an intermediate or connecting portion 51a extending from the other end of the coil 48b and terminating in a hook 74 that engages a tie wing. As illustrated in FIG. 11, the hook 74 engages around the tie wing 23 to anchor the spring to the bracket. It will be appreciated that there is ample room for the hook to be received behind the tie wing tips along with the ligature 36. Once the spring is activated and connected to the archwire as shown in FIG. 11, it will cause a counterclockwise movement of the bracket relative to the archwire. Otherwise, the spring 15B embraces the feature of the other embodiments in disposing the power coil 48b at the labial of the bracket for maximum aesthetics and hygiene. It will be further appreciated that the spring 15B may also be mounted to a multi-winged bracket where it may be anchored lingually to any of the tie wing tips depending upon the objective desired.

The embodiment of FIG. 13 differs from the embodiment of FIGS. 11 and 12 only in that the tail is connected to or engaged with one tie wing tip. In this regard the tail has a nearly closed loop 78 which nearly surrounds one of the tie wing tips.

It should be understood that the spring of each embodiment would be made in two forms (mirror images of each other) to produce either clockwise or counterclockwise uprighting movement with the connecting portion over the occlusal or incisal edge of the bracket.

It will be understood that modifications and variations may be effected without departing from the scope of the novel concepts of the present invention, but it is understood that this application is to be limited only by the scope of the appended claims.

The invention is hereby claimed as follows:

1. An uprighting spring for use with an orthodontic bracket having an archwire slot, an archwire secured in said slot and a vertically extending opening at one side of said archwire slot, said spring comprising a coil, an arm terminating in a hook and connected to one end of the coil, and a tail or leg connected to the other end of the coil, said coil being disposed between the arm and leg, said tail or leg adapted to extend through said opening to anchor one end of the spring, said hook on said arm being adapted to engage the archwire and activate the spring, and said coil, arm and leg being arranged and positioned relative to the bracket such that said coil is disposed at the labial of said bracket and generally within the labial profile of the bracket to thereby compact the overall profile of the bracket and spring.

2. The uprighting spring of claim 1, wherein the archwire slot is horizontally opening.

3. The uprighting spring of claim 1, wherein the archwire slot is horizontally opening and shaped to permit tipping and uprighting movements.

4. The uprighting spring of claim 1, wherein the archwire slot is vertically opening.

5. The uprighting spring of claim 1, which further includes an intermediate portion between the coil and tail extending over the gingival end of the bracket.

6. The uprighting spring of claim 1, which further includes an intermediate portion between the coil and tail extending over the occlusal end of the bracket.

7. The uprighting spring of claim 6, wherein the intermediate portion extends from the labial side of the coil.

8. The uprighting spring of claim 1, wherein the arm extends from the coil in substantial alignment with the archwire.

9. The uprighting spring of claim 1, wherein the tail is of such a length that the free end can be bent over one end of the bracket to prevent withdrawal of the tail from the opening.

10. An uprighting spring for use with an edgewise bracket having a horizontally opening archwire slot, and a vertically extending opening, said spring comprising a coil adapted to be disposed at the labial side of the bracket opposite the attaching side and over the archwire slot and generally within the labial profile of the bracket, a lever arm extending from one end of the coil terminating in a hook that is adapted to engage an archwire secured in the archwire slot of the bracket, a connecting portion extending from the other end of the coil and adapted to extend over and closely adjacent one end of the bracket, and a tail extending from the connecting portion and adapted to be received in said vertically extending opening to anchor the spring to the bracket, whereby the overall profile of the bracket and spring is compact.

11. The uprighting spring of claim 10, wherein the connecting portion overlies the gingival end of the bracket.

12. The uprighting spring of claim 10, wherein the connecting portion overlies the occlusal end of the bracket.

13. The uprighting spring of claim 12, wherein the connecting portion extends from the labial side of the coil.

14. The uprighting spring of claim 10, wherein the tail is of such a length that the free end can be bent over one end of the bracket to prevent withdrawal of the tail from the opening.

15. The uprighting spring of claim 10, wherein said lever arm extends substantially in alignment with said archwire.

16. An upright spring for use with a ribbon arch bracket having a vertically opening archwire slot that will accommodate crown tipping and root uprighting movements, and a vertically extending opening, said spring comprising a coil adapted to be disposed at the labial side of the bracket opposite the attaching side and generally within the labial profile of the bracket, a lever arm extending from one end of the coil terminating in a hook that is adapted to engage an archwire secured in the archwire slot of the bracket, a connecting portion extending from the other end of the coil and adapted to extend closely adjacent to and over one end of the bracket, and a tail extending from the connecting portion and adapted to be received in said vertically extending opening to anchor the spring to the bracket, whereby the overall profile of the bracket and spring is reduced.

17. The uprighting spring of claim 16, wherein the connecting portion overlies the gingival end of the bracket.

18. The uprighting spring of claim 16, wherein the connecting portion overlies the occlusal end of the bracket.

19. The uprighting spring of claim 16, wherein said lever arm extends substantially in alignment with said archwire.

20. The uprighting spring of claim 17, wherein the connecting portion extends from the labial side of the coil.

21. An uprighting spring for use with an edgewise bracket having a horizontally opening archwire slot and at least one tie wing having upper and lower tie wing tips, said spring comprising a coil adapted to be disposed at the labial side of the bracket opposite the attaching side and generally within the labial profile thereof, a lever arm extending from one end of the coil terminating in a hook that is adapted to engage an archwire secured in the archwire slot of the bracket, a connecting portion extending from the other end of the coil, and tail means extending from the connecting portion engaging the bracket and anchoring one end of the coil to the bracket, whereby the spring coil, lever arm connecting portion and tail coact with the bracket to compact the overall profile of the bracket and spring and enhance hygiene and aesthetics.

22. The uprighting spring of claim 21, wherein said tail means is straight and received in a vertical opening of the bracket.

23. The uprighting spring of claim 21, wherein said tail means is hook-shpaed and engages the tie wing.

24. An uprighting spring for use with an edgewise bracket having a horizontally opening archwire slot and at least one tie wing having opposed tie wing tips, said spring comprising an activating coil, means connecting one end of the coil to the archwire at one side of the bracket, and a tail extending from the other end of the coil to engage the bracket, whereby a clockwise or counter-clockwise uprighting movement is established between the bracket and the archwire, and said coil, lever arm and tail being constructed to dispose the coil at the labial of the bracket in substantial horizontal alignment with the archwire slot and generally within the labial profile of the bracket to thereby reduce the overall profile of the bracket and spring to provide maximum aesthetics and hygiene.

25. An uprighting spring for use with an orthodontic bracket having an archwire slot, an archwire secured in said slot, said spring comprising a force-generating means, means extending from the force-generating means for engagement with the bracket, and means extending from the force-generating means to engage the archwire, said force-generating means generating a force between said bracket and archwire and being disposed on the labial of the bracket over the archwire slot and generally within the labial profile of the bracket, whereby the spring forcegenerating means, bracket engaging means and archwire engaging means coact with the bracket to compact the overall profile of the bracket and spring.

26. An uprighting spring for use with an orthodontic bracket having an archwire slot and an archwire secured in said slot to generate an uprighting force between the bracket and the archwire, said spring comprising a coil, means at one end of the coil for connecting the coil to the archwire and means at the other end of the coil for connecting the coil to the bracket, and said coil, archwire connecting means and bracket connecting means being arranged with respect to each other and with respect to the bracket such that the coil is disposed at the labial or front side of the bracket and substantially within the labial profile of the bracket to thereby compact the overall profile of the bracket and the spring for enhancing aesthetics and hygiene.

* * * * *

UNITED STATES PATENT AND TRADEMARK OFFICE
CERTIFICATE OF CORRECTION

PATENT NO. : 4,842,514

DATED : June 27, 1989

INVENTOR(S) : PETER C. KESLING

It is certified that error appears in the above-identified patent and that said Letters Patent is hereby corrected as shown below:

Col. 3, line 13, change "or" to --of--;
Col. 5, line 43, delete the first occurrence of "of";
        last line, change "53" to --63--; and
Col. 7, line 55, change "upright" to --uprighting--.

Signed and Sealed this

Tenth Day of April, 1990

Attest:

HARRY F. MANBECK, JR.

*Attesting Officer*   *Commissioner of Patents and Trademarks*